(12) United States Patent
Frater (10) Patent No.: US 8,312,875 B2
(45) Date of Patent: Nov. 20, 2012

(54) FASTENABLE CONDUIT FOR BREATHABLE GAS DELIVERY

(75) Inventor: Robert Henry Frater, Lindfield (AU)

(73) Assignee: ResMed Limited, Bella Vista (AU)

( * ) Notice: Subject to any disclaimer, the term of this patent is extended or adjusted under 35 U.S.C. 154(b) by 1350 days.

(21) Appl. No.: 12/007,579

(22) Filed: Jan. 11, 2008

(65) Prior Publication Data
US 2008/0173305 A1 Jul. 24, 2008

Related U.S. Application Data

(60) Provisional application No. 60/879,798, filed on Jan. 11, 2007.

(51) Int. Cl.
*A61M 11/00* (2006.01)

(52) U.S. Cl. ............... 128/200.24; 128/204.18; 138/129

(58) Field of Classification Search ............. 128/200.24, 128/204.18; 138/128, 120, 129, 154, 162, 138/156
See application file for complete search history.

(56) References Cited

U.S. PATENT DOCUMENTS

| | | | |
|---|---|---|---|
| 4,695,955 A | 9/1987 | Faisandier | |
| 4,768,496 A | 9/1988 | Kreizman et al. | |
| 4,944,310 A | 7/1990 | Sullivan | |
| 5,813,404 A | 9/1998 | Devlin et al. | |
| 6,085,801 A * | 7/2000 | Lennartsson | 138/154 |
| 6,142,949 A | 11/2000 | Ubby | |
| 6,904,941 B2 * | 6/2005 | Howard | 138/167 |
| 6,910,483 B2 | 6/2005 | Daly et al. | |
| 7,318,437 B2 | 1/2008 | Gunaratnam et al. | |
| 2003/0154981 A1 | 8/2003 | Spruiell | |
| 2003/0196662 A1 | 10/2003 | Ging et al. | |
| 2007/0045152 A1 | 3/2007 | Kwok et al. | |
| 2007/0215228 A1 * | 9/2007 | Gosis et al. | 138/129 |
| 2010/0212768 A1 * | 8/2010 | Resendes | 138/116 |

FOREIGN PATENT DOCUMENTS

| | | |
|---|---|---|
| DE | 4020522 | 1/1992 |
| WO | 2004/060443 | 7/2004 |
| WO | 2006/125252 | 11/2006 |
| WO | PCT/AU2006/001169 | 2/2007 |

OTHER PUBLICATIONS

U.S. Appl. No. 11/988,809, filed Jan. 15, 2008 which is the National Phase of PCT/AU2006/001169 listed above.

* cited by examiner

*Primary Examiner* — Steven Douglas (74) *Attorney, Agent, or Firm* — Nixon & Vanderhye P.C.

(57) ABSTRACT

A fastenable air delivery conduit includes a body portion having a supply end and a delivery end and a fastener that substantially extends from the supply end to the delivery end. The fastener, when engaged, forms the body portion into a fastened configuration, and when disengaged, forms the body portion into an unfastened configuration. The body portion defines a longitudinal axis when in the fastened configuration, and the fastener extends from the source end to the delivery end of the body portion at an angle that is non-parallel with the longitudinal axis of the conduit.

25 Claims, 9 Drawing Sheets

FASTENABLE CONDUIT FOR BREATHABLE GAS DELIVERY

CROSS-REFERENCE TO RELATED APPLICATIONS

This application claims the benefit of U.S. Provisional Application No. 60/879,798, filed Jan. 11, 2007, which is incorporated herein by reference in its entirety.

FIELD OF THE INVENTION

The present invention relates to a fastenable conduit for delivering breathable air to a human when used with, for example, a continuous positive airway pressure (CPAP) system, or other positive pressure device.

BACKGROUND OF THE INVENTION

While several types of air delivery conduits exist for use in delivering pressurized air from a flow generator to a patient interface, conventional conduits have a size and shape that render them bulky to store and difficult to stow. The size and shape of conventional air delivery conduits are particularly inconvenient for those traveling with a Continuous Positive Airway Pressure (CPAP) system. Additionally, the size and shape of air delivery conduits renders them difficult to clean. As is understood in the art, cleanliness of the interior channel or core of air delivery conduits is desired for ensuring the health of patients using positive pressure systems or gas delivery devices.

A number of CPAP systems have been developed with the aim of achieving a more compact device. For example, U.S. patent application Ser. No. 11/483,564, incorporated herein by reference in its entirety, describes a storage system for a CPAP system that comprises a collapsible air delivery conduit having a z-shaped collapsible spring structure within the air passage. Moreover, International Pat. App. PCT/AU2006/001169, incorporated herein by reference in its entirety, describes a CPAP system comprising a compact air delivery conduit, such as an air delivery conduit that is unzippable into two distinct sections that can be retracted into a storage space.

There is a need for an improved, more compact, and fastenable air delivery conduit for use with positive pressure systems and gas delivery devices.

SUMMARY OF THE INVENTION

One aspect of the present invention is to overcome or at least substantially ameliorate one or more disadvantages of the prior art.

In one aspect, the present invention provides a fastenable air delivery conduit including a body portion having a supply end and a delivery end and a fastener system that substantially extends from the supply end to the delivery end. The fastener, when engaged, forms the body portion into a fastened configuration, and when disengaged, forms the body portion into an unfastened configuration. The body portion defines a longitudinal axis when in the fastened configuration, and the fastener extends from the source end to the delivery end of the body portion at an angle that is non-parallel with the longitudinal axis of the conduit.

In another aspect, the present invention provides a fastenable air delivery conduit including an unfastened body comprising first and second longitudinal edges, a first fastener that substantially extends along the first longitudinal edge of the unfastened body, and a second fastener that substantially extends along the second longitudinal edge of the unfastened body. The first fastener is adapted to engage the second fastener to form the unfastened body into a fastened conduit. The first and second fasteners comprise a tongue-in-groove arrangement.

In another aspect, the present invention provides a gas delivery system for use in CPAP therapy including a flow generator, a patient interface, and a fastenable air delivery conduit. The fastenable air delivery conduit includes a body portion having a supply end and a delivery end and a fastener that substantially extends from the supply end to the delivery end. The fastener, when engaged, forms the air delivery conduit into a fastened configuration, and when disengaged, forms the conduit into an unfastened configuration. The body portion defines a longitudinal axis when in the fastened configuration, and the fastener extends from the source end to the delivery end of the body portion at an angle that is non-parallel with the longitudinal axis of the conduit.

In another aspect, the present invention provides an air delivery conduit including a body having a supply end and a delivery end. At least a portion of the body is configurable between an unfastened configuration and a fastened configuration. The body is arranged such that in the unfastened configuration at least a portion of the body may be fastened to achieve the fastened configuration. The body defines a longitudinal axis when in the fastened configuration, and wherein the body is configurable between the unfastened configuration and the fastened configuration along an angle that is non-parallel with the longitudinal axis.

In another aspect, the present invention provides a method for cleaning an air delivery conduit including providing an air delivery conduit that is configurable between a first configuration in which an interior surface forms an interior core and a second configuration in which the interior core is open and the interior surface is exposed, converting the air delivery conduit into its second configuration, and cleaning the interior surface.

In another aspect, the present invention provides a method for storing an air delivery conduit including providing an air delivery conduit that is configurable between a first configuration to define an interior core and a second configuration to define a substantially planar configuration, converting the air delivery conduit into its second configuration, at least partially rolling and storing the air delivery conduit in its second configuration within a storage space, and cleaning the inside and/or outside surface of the air delivery conduit with one or more cleaning elements or modules provided to the storage space.

Of course, portions of the described aspects of the present invention may form sub-aspects of the present invention. Also, various ones of the sub-aspects and/or aspects may be combined in various manners and also constitute additional aspects or sub-aspects of the present invention. These and other features and aspects of the present invention will be described in or be apparent from the detailed description below read in conjunction with the attached figures.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The present invention provides an air delivery conduit for use with a positive pressure system or gas delivery device, such as, for example, a Continuous Positive Airway Pressure (CPAP) system. In particular, for example, the air delivery conduit can be adapted for use with the CPAP systems described in U.S. patent application Ser. No. 11/483,564 and in International Pat. App. Ser. No. PCT/AU2006/001169. Additionally, the air delivery conduit can be used with any respirator system or device, such as a portable ER respirator.

A conduit that is fastenable, in one broad sense, means that the conduit is convertible between fastened and unfastened configurations through engaging or disengaging of a fastener. In this regard, fastenable also means that a conduit in unfastened or open configuration can be fastened, closed, reconfigured, or engaged through use of a fastening system, to create a conduit in a sufficiently or substantially closed configuration that is useable for delivering air or other gas through an interior core, channel, or space defined by the fastened conduit. In another sense, the conduit is convertible between a collapsible position in which the conduit is substantially flat for storage and a patent position in which the conduit establishes a conduit for air delivery. In an embodiment, the conduit may not include a fastener and may be converted between collapsible and patent positions in other suitable manners.

Figure 1A:
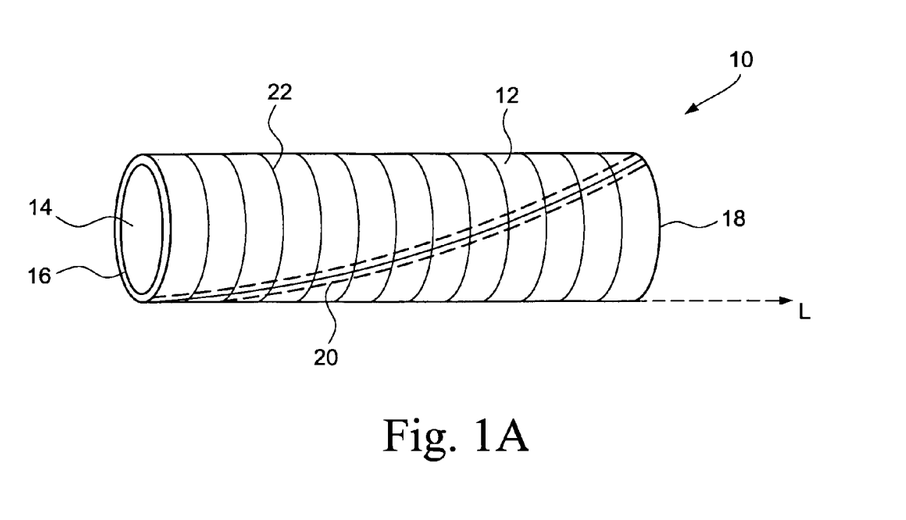
FIG. 1A is a perspective view of an air delivery conduit in accordance with an embodiment of the present invention, wherein the air delivery conduit is in a fastened configuration.
Figure 1B:
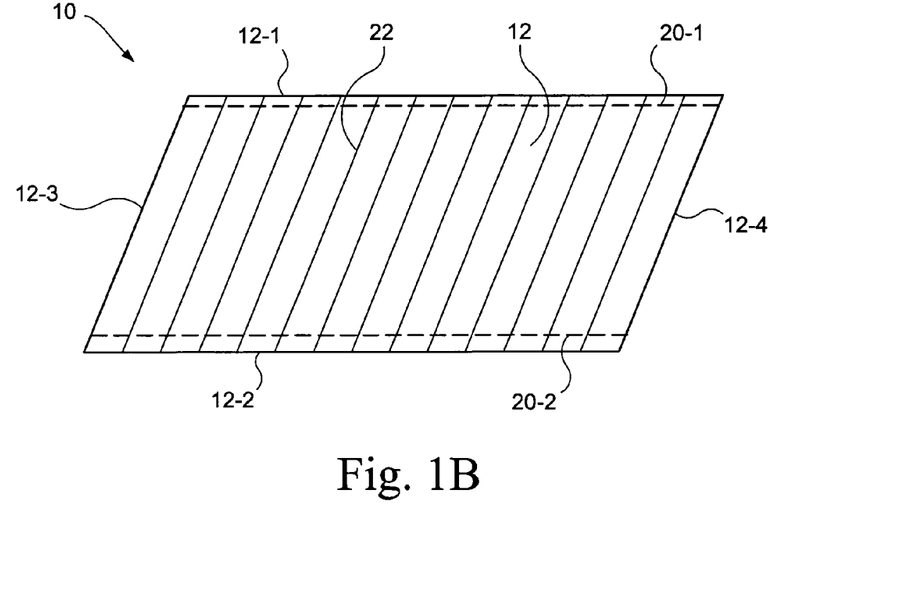
FIG. 1B is a top planar view of the air delivery conduit of FIG. 1A, wherein the air delivery conduit is in an unfastened configuration.
Figure 2A:
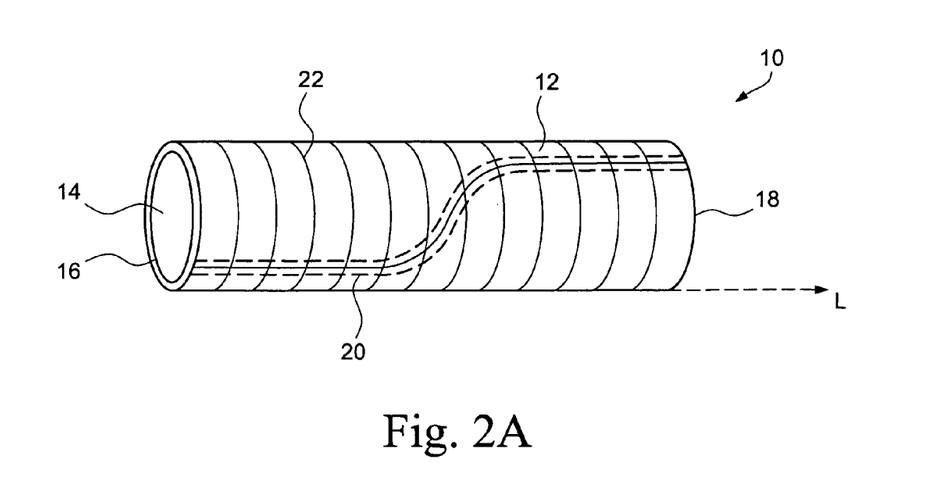
FIG. 2A is a perspective view of an air delivery conduit in accordance with another embodiment of the present invention, wherein the air delivery conduit is in a fastened configuration.
Figure 2B:
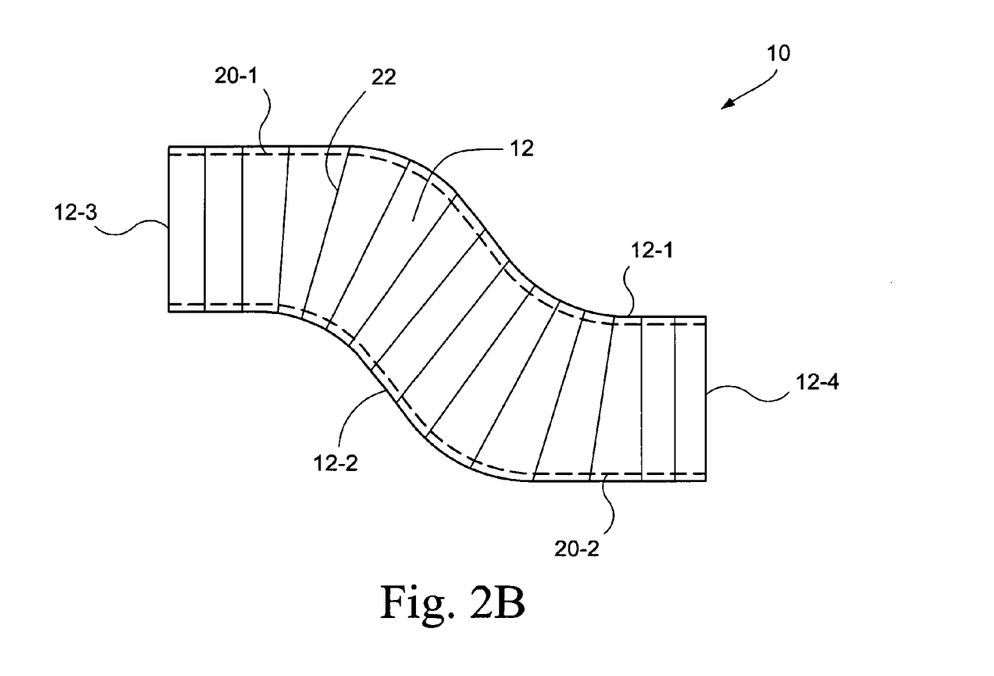
FIG. 2B is a top planar view of the air delivery conduit of FIG. 2A, wherein the air delivery conduit is in an unfastened configuration.
Figure 9:
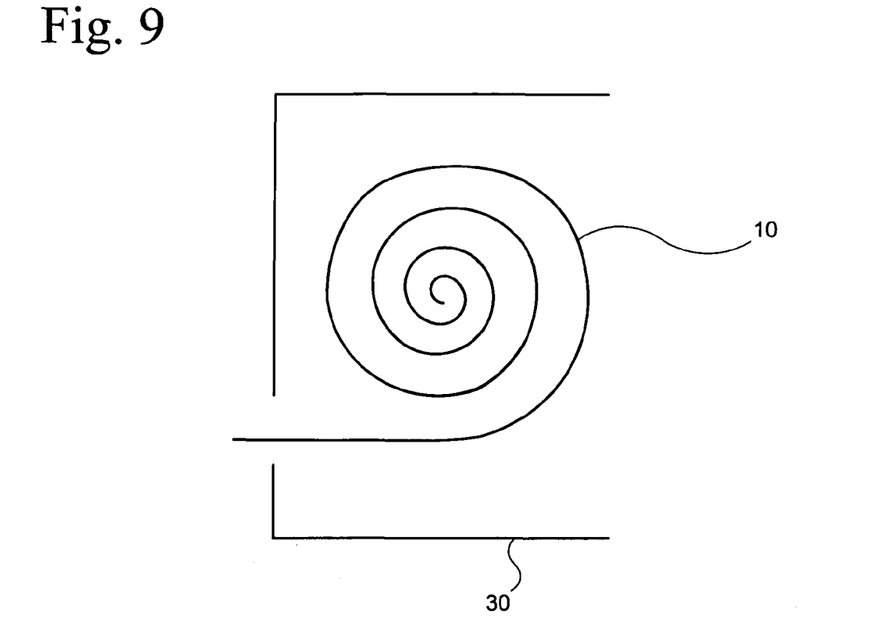
FIG. 9 is a side elevation view of an air delivery conduit, wherein the conduit is compacted within a storage space.

The air delivery conduit is convertible between different forms or configurations, through engaging or disengaging of the fastener. In one form, as is illustrated in FIGS. 1A and 2A, the fastener 20 of the air delivery conduit 10 is engaged and the air delivery conduit 10 exists in a fastened configuration having a longitudinal core 14 through which an air flow can pass. In another form, as is illustrated in FIGS. 1B and 2B, the fastener 20 of the air delivery conduit 10 is disengaged and the air delivery conduit 10 exists in an unfastened configuration that renders the air delivery conduit 10 more compact, more stowable, more suitable for travel, more transportable, more packageable for sale, and/or more cleanable. In some embodiments, the air delivery conduit 10, when in an unfastened configuration can be further compacted, such as, for example, by rolling the unfastened air delivery conduit from source end 16 to delivery end 18, or vice versa. FIG. 9, for example, illustrates an embodiment in which an air delivery conduit 10 has been rolled and stored within a storage space 30, such as, for example, a flow generator. In this regard, the air delivery conduit 10, when in an unfastened configuration, can be further compacted to any desired extent. In one embodiment, for example, an air delivery conduit that is 2 meters long and that, in a fastened configuration, has a diameter of 20 mm, can be compacted to a size less than about 500 $cm^3$ (e.g., less than about 475 $cm^3$, less than about 450 $cm^3$, less than about 425 $cm^3$, less than about 400 $cm^3$, less than about 375 $cm^3$, less than about 350 $cm^3$, less than about 325 $cm^3$, less than about 300 $cm^3$, less than about 275 $cm^3$, less than about 250 $cm^3$, less than about 225 $cm^3$, less than about 200 $cm^3$, less than about 175 $cm^3$, less than about 150 $cm^3$, less than about 125 $cm^3$, or even less than about 100 $cm^3$). The cubic volume that the compactable conduit takes up, in this regard, will depend upon the length of the conduit, the diameter of the conduit when in a fastened configuration, and whether there are other portions of the conduit, such as end portions, that do not open up or lend themselves to being further compactable.

The overall volume of the delivery conduit 10, in this regard, can be decreased when changed from a fastened configuration to an unfastened configuration by greater than about 90%, such as, for example, by greater than about 80%, by greater than about 70%, by greater than about 60%, by greater than about 50%, by greater than about 40%, by greater than about 30%, by greater than about 20%, or even by greater than about 10%. In some embodiments, the volume of the air delivery conduit 10, when unfastened and further compacted from a fastened configuration, can be decreased from about 10 to about 90%, such as, for example, from about 20 to about 80%, from about 30 to about 80%, from about 40 to about 80%, or even from about 40 to about 70%. In one embodiment, for example, an air delivery conduit that is 2 meters long and that, in a fastened configuration, has a diameter of 20 mm, the volume of the air delivery conduit 10 can be decreased from an initial volume of about 650 cm$^3$ to final volume of about 400 cm$^3$, about 375 cm$^3$, about 350 cm$^3$, about 325 cm$^3$, about 300 cm$^3$, about 275 cm$^3$, about 250 cm$^3$, about 225 cm$^3$, about 200 cm$^3$, about 175 cm$^3$, about 150 cm$^3$, about 125 cm$^3$, or even about 100 cm$^3$.

In FIGS. 1A, 2A, 3B, and 4, an air delivery conduit 10 in a fastened configuration is illustrated. The air delivery conduit 10 comprises a body portion 12 having a source end 16, a delivery end 18, and a longitudinal core 14 that extends from the source end 16 to the delivery end 18. The air delivery conduit 10 also comprises a fastener 20 that extends from the source end 16 to the delivery end 18 of the air delivery conduit 10. Additionally, the air delivery conduit 10 comprises a series of ribs or corrugations 22 that are situated along the extent of the air delivery conduit 10 from the source end 16 to the delivery end 18 of the air delivery conduit 10.

In FIGS. 1B and 2B, an air delivery conduit 10 in an unfastened configuration is illustrated. Here, the fastener is illustrated as comprising a first fastening element 20-1 and a second fastening element 20-2 that are disengaged from each other, wherein the first fastening element 20-1 and the second fastening element 20-2 are situated on opposing longitudinal edges 12-1 and 12-2 of the body portion 12. The air delivery conduit 10 also comprises a source edge 12-3 and a delivery edge 12-4 that, when the fastener 20 is engaged, form the source end 16 and delivery end 18 discussed above with respect to FIGS. 1A, 2A, 3B and 4. Additionally, the air delivery conduit 10 comprises a series of ribs or corrugations 22 that are situated along the extent of the air delivery conduit 10 from the source end 16 to the delivery end 18 of the air delivery conduit 10.

Construction of Conduit

The air delivery conduit 10 can comprise any suitable material. In particular, for example, the air delivery conduit 10 can comprise a flexible and/or resilient material, such as a polymer material, a polymer-like material, a plastic, plastic-like, rubber, fabric (e.g., impregnated fabric, such as plastic-impregnated fabric). The conduit can also comprise any health-, medical-, or pharmaceutical-grade (e.g., pharmaceutically-acceptable) material, such as, for example, polyethylene, polypropylene, polyolefins, silicones, Gortex®, and the like. In one preferred embodiment, the air delivery conduit 10 is structured such that the interior or internal surface of the body portion 12 of the conduit is substantially smooth. The smooth interior surface of the conduit, in this regard, is preferably of sufficient smoothness to prevent or minimize air flow friction and/or air flow turbulence during the passage of an air or gas flow through the conduit. It is also desirable to minimize noise or sound caused by air flow through the conduit. It should be understood, however, that the interior surface of the air delivery conduit 10, or portions thereof, can have any desired degree of smoothness. Alternatively, or in addition, the exterior surface of the air delivery conduit 10 is substantially soft and/or substantially smooth, such that the air delivery conduit 10 can slide across furniture, bed linens, etc. in a desirable manner. It should be understood that the exterior surface of the air delivery conduit 10, or portions thereof, can have any desired degree of softness and smoothness. In some embodiments, for example, it may useful to have certain portions of the outer surface to be sticky or fastenable so the conduit may be held in place.

The air delivery conduit 10 can be any suitable size, such as, for example, a size that is suitable for use with a positive pressure system or gas delivery device (e.g., a CPAP system). In particular, for example, the air delivery conduit 10 can have a diameter, when in fastened configuration with fastener 20 engaged, of less than about 40 mm, such as, for example, a diameter of less than about 35 mm, less than about 30 mm, less than about 25 mm, less than about 22 mm, less than about 20 mm, less than about 18 mm, less than about 15 mm, or even less than about 10 mm. In some embodiments, the air delivery conduit 10 can have a diameter from about 10 mm to about 40 mm, such as, for example, from about 10 mm to about 30 mm, from about 10 mm to about 20 mm, from about 12 mm to about 30 mm, from about 12 mm to about 20 mm, from about 16 mm to about 30 mm, or even from about 16 mm to about 25 mm. In use, the air delivery conduit 10 may automatically expand to the required diameter due to the introduction of pressurized air to provide a substantially rigid tube for allowing the passage of air therethrough. The air delivery conduit 10 can also be any suitable length, such as, for example, a length greater than about 1 m, greater than about 1.5 m, greater than about 2 m, greater than about 2.5 m, greater than about 3 m, greater than about 3.5 m, or even greater than about 4 m. It is even suitable for the air delivery conduit 10 to have a length from about 1 m to about 4 m, such as, for example, from about 1 m to about 3 m, from about 1.5 m to about 4 m, from about 1.5 m to about 3 m, from about 2 m to about 4 m, from about 2 m to about 3.5 m, or even from about 2 m to about 3 m. The air delivery conduit 10 can also have any suitable wall thickness, such as, for example, a wall thickness from about 0.01 mm to about 2 mm, e.g., from about 0.05 mm to about 1.5 mm, from about 0.1 mm to about 1.25 mm, or even from about 0.2 mm to about 1.0 mm.

The source end 16 and delivery end 18 of the air delivery conduit 10 can be of any suitable size and structure for coupling in a sufficiently air-tight manner (e.g., via snap-fit, snug-fit, or detent) to a flow generator 40 and to a patient interface 50, respectively, or to connectors, interconnectors, or couplers thereto. In some embodiments, the source end 16 and/or delivery end 18 can be fitted with removable end caps (not illustrated) that are adapted to be engaged to a flow generator and to a patient interface, respectively, or to connectors, interconnectors, or couplers thereto. In another embodiment, the source end 16 of the air delivery conduit 10 is adapted to engage a patent interface connector for use in coupling one end of the air delivery conduit 10 to a patient interface, and/or the delivery end is adapted to engage a flow generator connector for use in coupling the delivery end of the air delivery conduit 10 to a flow generator. It should be understood, in this regard, that the air delivery conduit 10 can be adapted to couple with any suitable coupler device (e.g., coupler devices comprising recognition systems), such as described, for example, in International Pat. App. Ser. No. PCT/AU2006/001169.

The air delivery conduit 10, when in a fastened configuration, can have any shape that is suitable for gas delivery. In particular, it should be understood that the air delivery conduit 10 can have any suitable cross-sectional shape. In certain embodiments, for example, the air delivery conduit 10 comprises a round, circular, ovular, oblong, or irregularly-shaped cross sectional shape. In other embodiments, the air delivery conduit 10 comprises a more angular cross-sectional shape, such as, for example, an angular cross sectional shape that lacks sharp edges. Additionally, the air delivery conduit can be comprise any suitable lengthwise shape, such as, for example, straight, curved, bent, or a mixture thereof. As discussed below with respect to the fastener element, the shape of the air delivery conduit, when in an unfastened configuration is dependent on the orientation of the fastener on or in the body portion of the air delivery conduit. In particular, for example, the air delivery conduit can be substantially trapezoidal in shape when in unfastened configuration, as depicted, for example, in FIG. 1B. Alternatively, the air delivery conduit can be substantially rectangular or square in shape, when in an unfastened configuration. It is even possible for the air delivery conduit to be irregularly shaped (e.g., having only two parallel edges, or no parallel edges) when in an unfastened configuration, as is illustrated, for example, in FIG. 2B.

Ribs, Corrugations, and Structural Support Elements

Figure 8A:
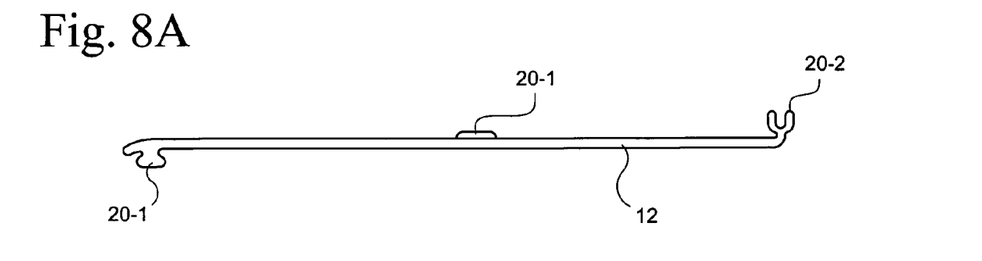
FIG. 8A is a side elevation view of an air delivery conduit in accordance with another embodiment of the present invention, wherein the air delivery conduit is in an unfastened configuration.
Figure 8B:
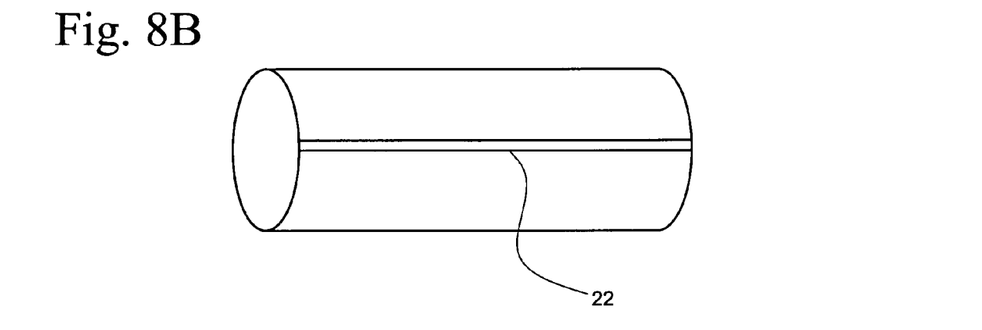
FIG. 8B is a perspective view of an air delivery conduit in accordance with another embodiment of the present invention, wherein the air delivery conduit is in a fastened configuration.
Figure 8C:
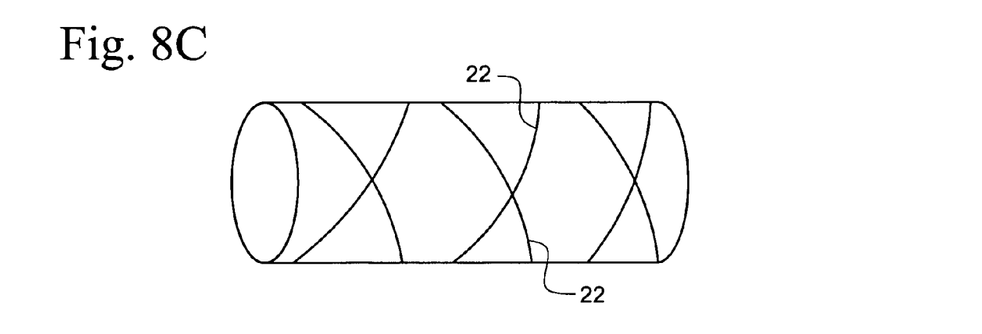
FIG. 8C is a perspective view of an air delivery conduit in accordance with another embodiment of the present invention, wherein the air delivery conduit is in a fastened configuration.
Figure 8D:
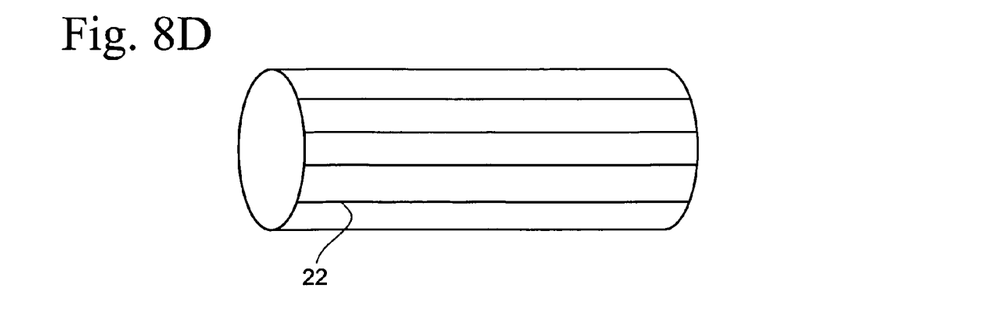
FIG. 8D is a perspective view of an air delivery conduit in accordance with another embodiment of the present invention, wherein the air delivery conduit is in a fastened configuration.

The air delivery conduit 10 further comprises one or more ribs, corrugations, and/or structural elements 22 to reinforce, strengthen, enhance resiliency and/or flexibility of, and/or to prevent kinking and/or collapse of the air delivery conduit 10. The rib, corrugation, and/or structural elements 22 can be present in any suitable size, shape, and orientation. It is suitable, for example, for ribs, corrugations and/or structural elements to be oriented in a substantially perpendicular, substantially parallel, angular (e.g., diagonal), or curved manner as compared to longitudinal axis L of the air delivery conduit 10 (illustrated in FIGS. 1A and 2A). The ribs, corrugations, and/or structural elements, in this regard, can be situated at any angle as compared to longitudinal axis L of the air delivery conduit 10, such as, for example, at an angle less than about 90 degrees, less than about 80 degrees, less than about 70 degrees, less than about 60 degrees, less than about 50 degrees, less than about 40 degrees, less than about 30 degrees, less than about 20 degrees, or even less than about 10 degrees as compared to longitudinal axis L of the air delivery conduit 10. Additionally, the ribs, corrugations, and/or structural elements 22 can comprise any suitable material (e.g., the same material as that of the body portion 12, but in greater thickness, or at least one different material, such as a material have greater resiliency or a material having lesser flexibility). In this regard, for example, the ribs, corrugations, and/or structural elements 22 can comprise any suitable health grade plastic or polymeric material. Additionally, the ribs, corrugations and/or structural elements 22 can distributed in any suitable manner in or on the air delivery conduit 22, such as, for example, in a uniform manner or in a non-uniform, dispersed manner (e.g., at sites of desired bending of the air delivery conduit 10). In one embodiment, as is illustrated in FIGS. 1A, 1B, 2A, 2B, 4, and 5, the air delivery conduit 10 comprises a series of ribs or corrugations 22 that are situated along the extent of the air delivery conduit 10 from the source end 16 to the delivery end 18, and which are oriented in a substantially perpendicular manner with respect to longitudinal axis L of the air delivery conduit 10 (illustrated in FIGS. 1A and 2A). In another embodiment, as is illustrated in FIGS. 8A, 8B, and 8D, the air delivery conduit 10 comprises one or more ribs or corrugations 22 that are oriented in a substantially parallel manner with respect to longitudinal axis L of the air delivery conduit 14. In another embodiment the air delivery conduit comprises ribs or corrugations that are oriented in a substantially diagonal orientation with respect to the longitudinal axis L of the air delivery conduit 10, in order to increase flexibility of the conduit. In yet another embodiment, as is illustrated in FIG. 8C, the air delivery conduit comprises ribs or corrugations 22 that are oriented at more than one different angle as compared to longitudinal axis L of the air delivery conduit 10, such as, for example, to form a web- or matrix-like structure. In yet another embodiment, the air delivery conduit comprises a non-uniform distribution of structural elements that are oriented in a substantially parallel manner with respect to the longitudinal axis L of the air delivery conduit 10. In another embodiment, the air delivery conduit comprises rib elements that spiral substantially around the outer surface of the air delivery conduit.

Fastener

Figure 5:
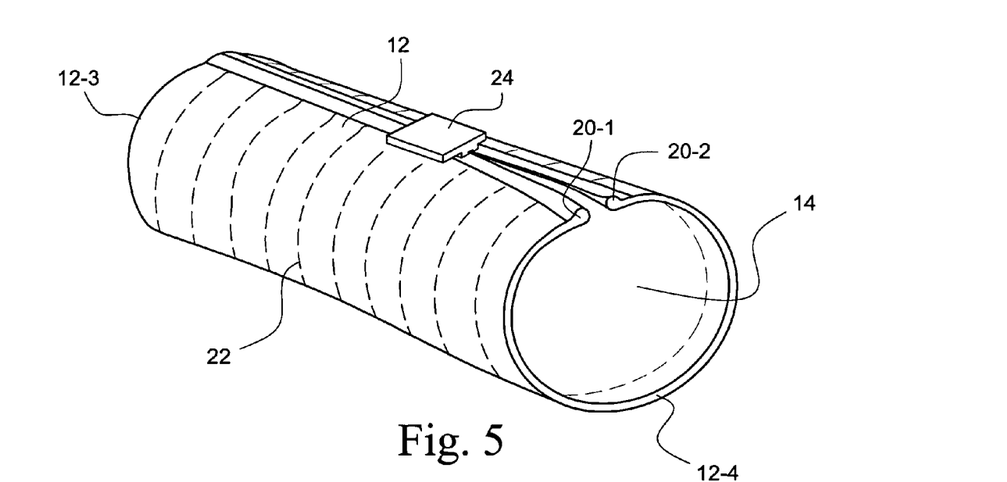
FIG. 5 is a perspective view of an air delivery conduit in accordance with another embodiment of the present invention, wherein the fastener is partially disengaged.

The fastener 20 can be any suitable fastening system that is engagable and disengagable to enable the fastenability and unfastenability features of the air delivery conduit 10 described herein. The fastener 20, in this regard, can comprise any structure that is suitable for substantially providing or providing a sufficiently air-tight and/or sufficiently leak-proof seal. As illustrated in FIGS. 1B, 2B and 5, the fastener 20 can comprise a first fastening element 20-1 and a second fastening element 20-2, wherein the first fastening element is adapted to engage the second fastening element. The first and second fastening elements, in this regard, can comprise any suitable corresponding or mating structures that, when coupled or engaged, cause or enable the air delivery conduit 10 to be in a fastened configuration. In some embodiments, the first and second fastening elements comprise any suitable corresponding or mating structures that, when coupled or engaged, render the fastener 20 sufficiently air-tight for the air delivery conduit 10 to act as a conduit for air delivery.

Figure 3A:
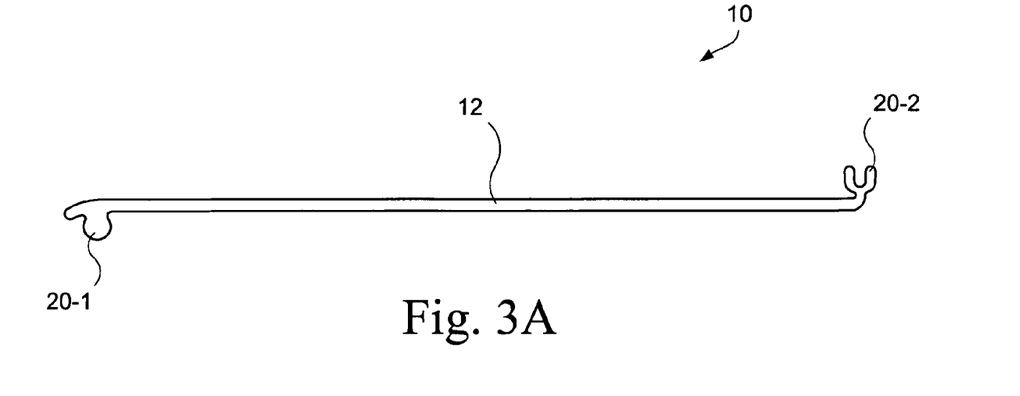
FIG. 3A is a side elevation view of an air delivery conduit in accordance with another embodiment of the present invention, wherein the air delivery conduit is in an unfastened configuration.
Figure 3B:
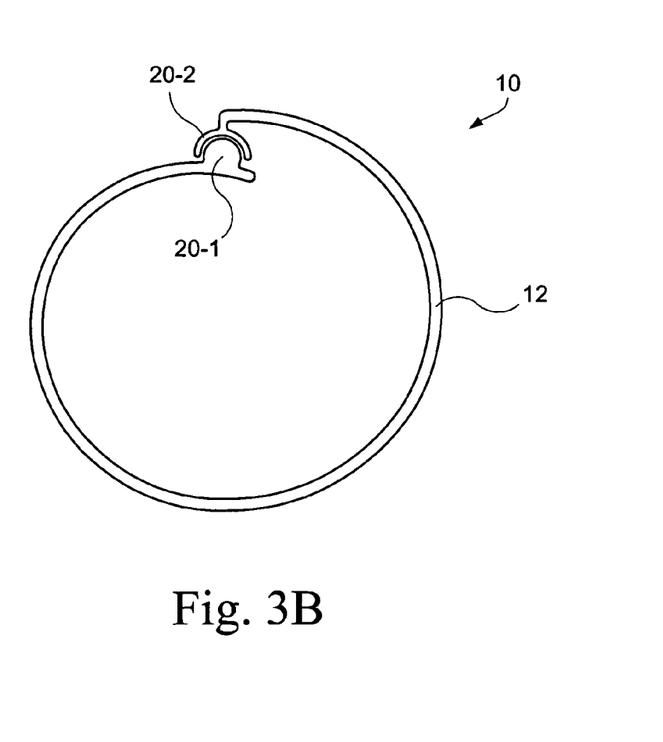
FIG. 3B is a side elevation view of the air delivery conduit of FIG. 3A, wherein the air delivery conduit is in a fastened configuration.
Figure 4:
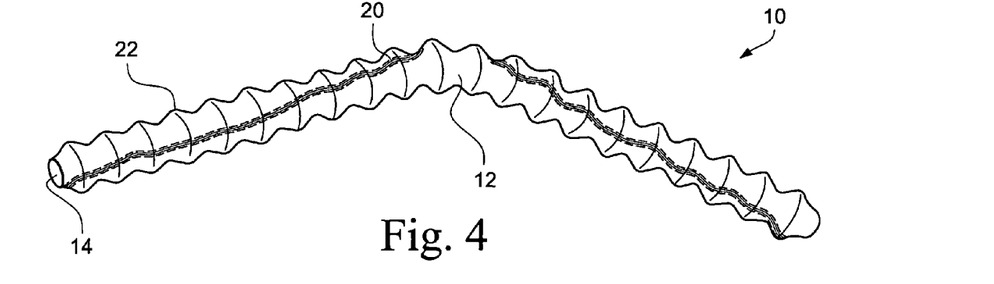
FIG. 4 is a perspective view of an air delivery conduit in accordance with another embodiment of the present invention.
Figure 6:
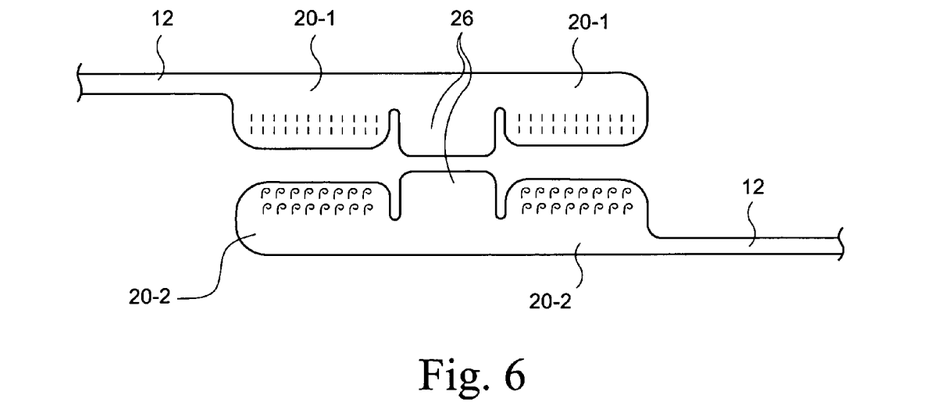
FIG. 6 is a side elevation view of a fastener that is suitable for use with an embodiment of the present invention.
Figure 7A:
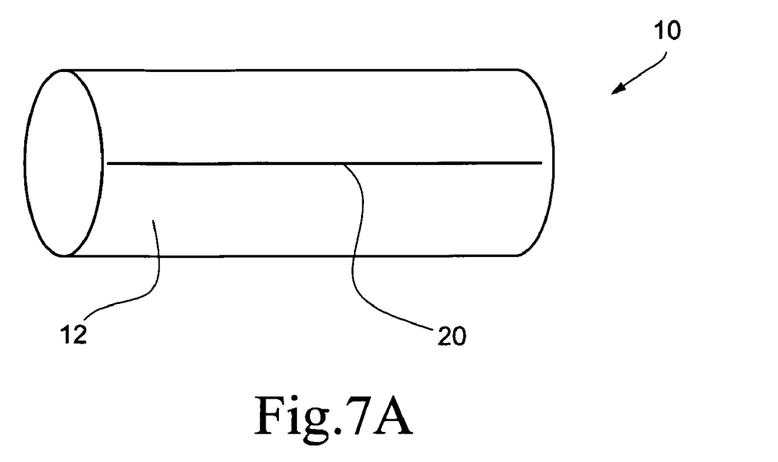
FIG. 7A is a perspective view of an air delivery conduit in accordance with another embodiment of the present invention, wherein the air delivery conduit is in a fastened configuration.
Figure 7B:
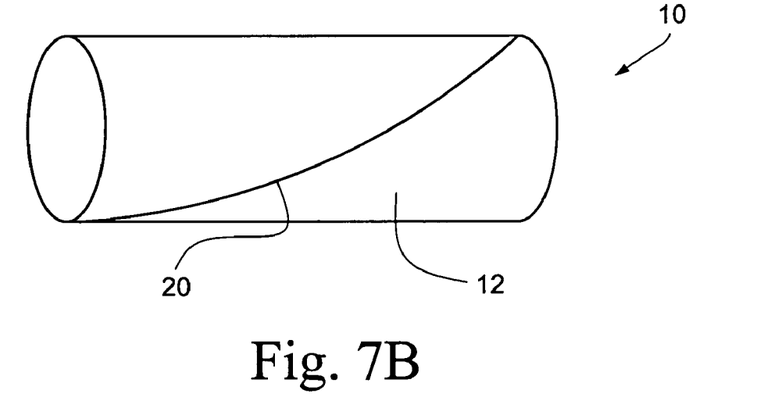
FIG. 7B is a perspective view of an air delivery conduit in accordance with another embodiment of the present invention, wherein the air delivery conduit is in a fastened configuration.
Figure 7C:
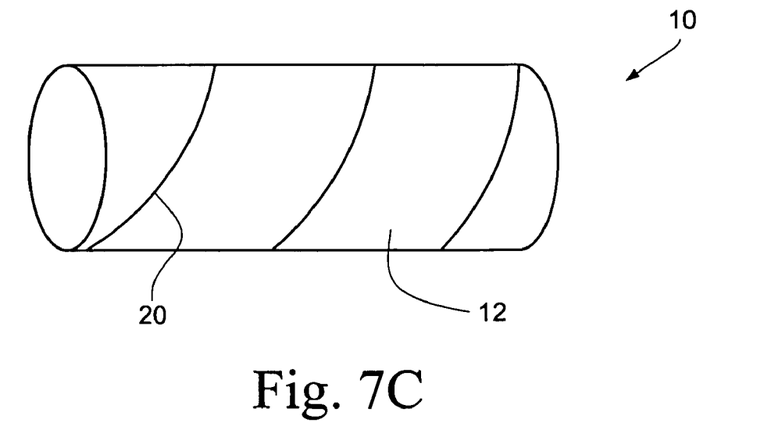
FIG. 7C is a perspective view of an air delivery conduit in accordance with another embodiment of the present invention, wherein the air delivery conduit is in a fastened configuration.

In one embodiment, as illustrated in FIGS. 3A and 3B, for example, the fastener 20 can comprise a tongue-in-groove structure, wherein the first fastening element 20-1 is adapted to engage the second fastening element 20-2 without the use of a slidable locking mechanism. In another embodiment, as illustrated in FIG. 5, the fastener comprises a tongue-in-groove structure, wherein the first fastening element 20-1 is adapted to engage the second fastening element 20-2 through operation of a slidable locking mechanism 24. The fastener in FIG. 5 is illustrated in a partially disengaged position. In another embodiment, the fastener 20 comprises an interlocking rib and groove structure, such as, for example, a zipper (e.g., a water-proof zipper or an air-tight zipper). In another embodiment, as illustrated in FIG. 6, the fastener 20 comprises loop and hook Velcro™-type fastening elements. In particular, FIG. 6 illustrates the fastener 20 as comprising a first fastening element 20-1 that comprises two Velcro™-type hook-containing regions that are separated by a sealant region 26 comprising a sealing material, and a second fastening element 20-2 that comprises two Velcro™-type loop-containing regions that are separated by a sealant region 26 comprising a sealing material, wherein the first fastening element 20-1 is adapted to engage the second fastening element 20-2 in such a manner that the two hook-containing regions of the first fastening element 20-1 couple with the two loop-containing regions of the second fastening element 20-2, and the sealant regions 26 of the first and second fastening elements 20-1 and 20-2 overlap and collectively form a sufficiently air-tight and/or sufficiently leak-proof seal. In yet another embodiment, the first fastening element and/or the second fastening element of the fastener 20 comprise an adhesive, a zipper, velcro, a tongue-in-groove element, a soft seal, an interlocking rib and groove structure, or portions thereof, or combinations thereof.

Figure 1C:
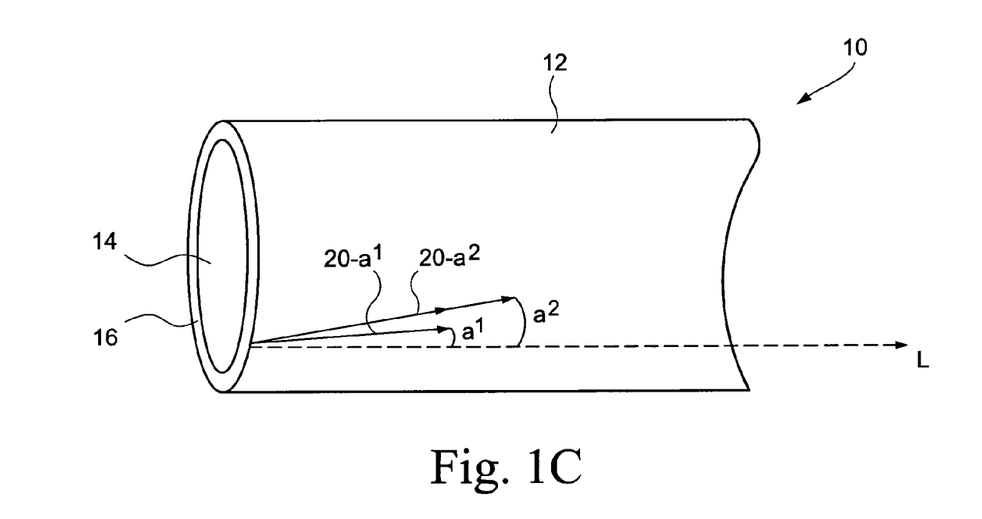
FIG. 1C is a perspective view of an air delivery conduit in accordance with another embodiment of the present invention, wherein fastener angles are depicted.
Figure 10:
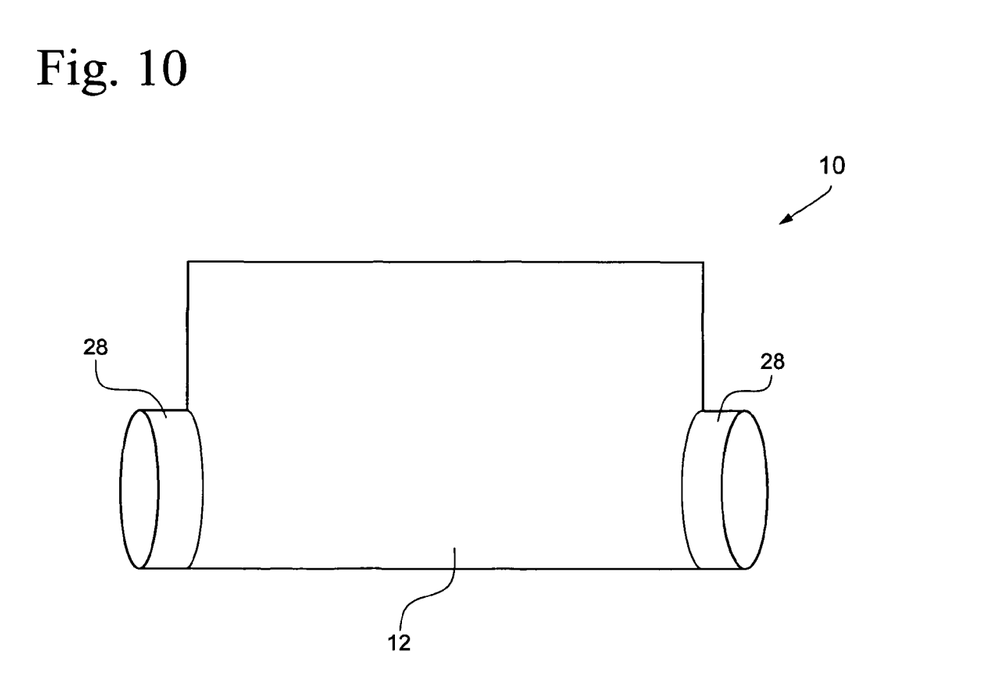
FIG. 10 is a perspective view of an air delivery conduit in accordance with another embodiment of the present invention, wherein the air delivery conduit has fixed collars and is in an unfastened configuration.
Figure 11:
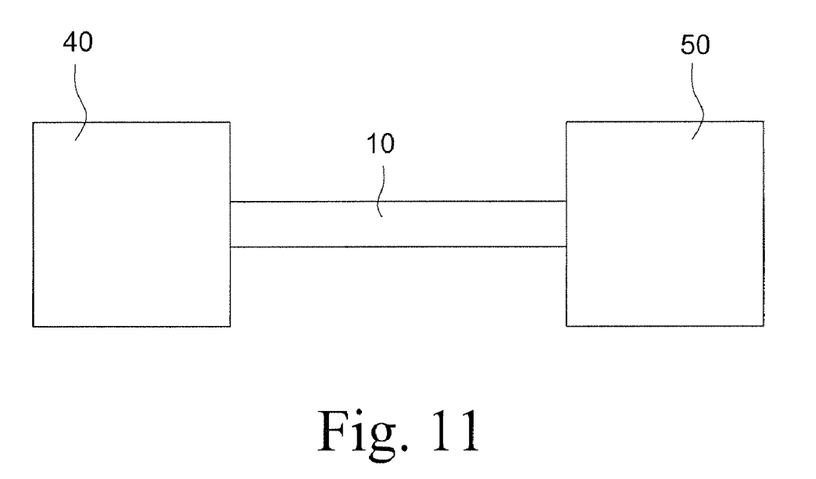
FIG. 11 is a schematic representation of an air delivery conduit connected to a flow generator and a patient interface in accordance with an embodiment of the present invention.

The first fastening element 20-1 and the second fastening element 20-2 can be oriented in any suitable manner with respect to the body portion 12 of the air delivery conduit 10, such that when the first and second fastening elements 20-1 and 20-2 are disengaged from each other, the air delivery conduit 10 exists in an unfastened configuration, and when the first and second fastening elements 20-1 and 20-2 are engaged with each other, the air delivery conduit 10 exists in a fastened configuration. As is illustrated in FIGS. 1A, 2A, 7A, 7B, and 7C, for example, the first fastening element 20-1 and the second fastening element 20-2 can extend from the source end 16 to the delivery end 18 of the air delivery conduit 10 in any continuous or intermittent manner. In one embodiment, as is illustrated in FIG. 10, the fastener extends between two fixed collars 28 at the source and delivery ends of the air delivery conduit 10. Additionally, as is illustrated in FIGS. 1A and 2A, for example, the first fastening element 20-1 and the second fastening element 20-2 can extend from the source end 16 to the delivery end 18 of the air delivery conduit 10 in any suitable coordinating angle or shape relative to longitudinal axis L of the air delivery conduit 10 (illustrated in FIGS. 1A and 2A). In one embodiment, for example, as is illustrated in FIG. 2A, the first and second fastening elements 20-1 and 20-2 collectively define a shaped (or S-shaped) fastener seam. In another embodiment, as is illustrated in FIG. 1A, the first and second fastening elements collectively define a diagonally-oriented fastener seam. As illustrated in FIG. 1C, the fastener 20 is oriented at any suitable angle relative to a longitudinal axis L (illustrated in FIGS. 1A, 1B, and 1C). The fastener 20, in this regard, can have any suitable diagonally-oriented angle relative to the longitudinal axis L of the air delivery conduit 10 (illustrated in FIGS. 1A, 1B, and 1C). FIG. 1C, for example, illustrates two example fasteners 20-$a^1$ and 20-$a^2$ having two example angles $a^1$ and $a^2$ relative to the longitudinal axis L. In some embodiments, it is suitable for the fastener angle relative to the longitudinal axis of the air delivery conduit 10 to be such that the fastener 20 wraps around the circumferential edge of the air delivery conduit less than about six times (e.g., less than about five times, less than about four times, less than about three times, less than about two times, less than about 1 time) in the span of conduit between the source end 16 and the delivery end (not illustrated in FIG. 1C). In other embodiments, the fastener 20 is oriented at an angle between about 0.1 degrees and about 30 degrees relative to the longitudinal axis L of the air delivery conduit, such as, for example, at an angle between about 0.25 degrees and about 20 degrees, between about 0.5 degrees and about 15 degrees, between about 1 degree and about 12 degrees, or even between about 2 degrees and about 10 degrees, relative to the longitudinal axis L of the air delivery conduit. In yet another embodiment, the fastener 20 is oriented at an angle of less than about 40 degrees relative to the longitudinal axis L of the air delivery conduit, such as, for example, at an angle less than about 30 degrees, less than about 25 degrees, less than about 20 degrees, less than about 15 degrees, less than about 10 degrees, less than about 5 degrees, or even less than about 1 degree, relative to the longitudinal axis L of the air delivery conduit.

As will be understood, the flexibility of the air delivery conduit 10 can be increased or enhanced, in some embodiments, by orienting the fastener 20 at an angle relative to the longitudinal axis L of the air delivery conduit 10 (illustrated in FIGS. 1A and 2A) in its extension from the source end 16 to the delivery end 18, as compared to embodiments in which the fastener is substantially parallel with the longitudinal axis L. In some embodiments, for example, an air delivery conduit 10 having an approximately 12 inch long end portion thereof (either the source end 16 or the delivery end 18) suspended towards an imaginary horizontal axis will form an angle at the point of suspension of greater than about 10 degrees below the horizontal axis, such as, for example, an angle of greater than about 20 degrees, greater than about 30 degrees, greater than about 40 degrees, greater than about 50 degrees, greater than about 60 degrees, greater than about 70 degrees, or even greater than about 80 degrees below the horizontal axis (e.g., an angle between about 10 degrees and about 90 degrees, between about 20 degrees and about 80 degrees, between about 30 degrees and about 70 degrees, or even between about 40 degrees and about 60 degrees below the horizontal axis).

In one embodiment, the air delivery conduit 10, when in a fastened configuration with the first and second fastening elements 20-1 and 20-2 engaged, is capable of delivering an air flow having a pressure greater than about 5 cm $H_2O$ (e.g., greater than about 10 cm $H_2O$, greater than about 15 cm $H_2O$, greater than about 20 cm $H_2O$, greater than about 25 cm $H_2O$, or greater than about 30 cm $H_2O$) with no substantial leakage occurring at the engaged fastener 20 (e.g., a leakage of less than about 1-25 L/min at 10 cm $H_2O$, less than about 1-20 L/min at 10 cm $H_2O$, less than about 1-15 L/min at 10 cm $H_2O$, less than about 1-10 L/min at 10 cm $H_2O$, less than about 0.1-5 L/min at 10 cm $H_2O$, less than about 1-25 l/min at 15 cm $H_2O$, less than about 1-20 L/min at 15 cm $H_2O$, less than about 1-15 L/min at 15 cm $H_2O$, less than about 1-10 L/min at 15 cm $H_2O$, less than about 0.1-5 L/min at 15 cm $H_2O$, less than about 1-25 L/min at 20 cm $H_2O$, less than about 1-20 L/min at 20 cm $H_2O$, less than about 1-15 L/min at 20 cm $H_2O$, less than about 1-10 L/min at 20 cm $H_2O$, less than about 0.1-5 L/min at 20 cm $H_2O$) occurring at the fastener 20. It will be understood, in this regard, that the air delivery conduit 10 can be operably connected to any type of flow generator with substantially no leakage occurring at the fastener 20, such as, for example, with two-stage flow generators that may provide greater pressure rise and fall times.

Support Webs

The central core 14 of the air delivery conduit 10 can be substantially hollow and/or free of structural components. Alternatively, the air delivery conduit can comprise one or more support webs (not illustrated) to provide internal support for the air delivery conduit 10, as described, for example, in International Pat. App. Ser. No. PCT/AU2006/001169. In this regard, however, it is preferable that the support webs are positioned or oriented in such a manner that the air delivery conduit 10 is substantially planar or flat when the fastener 20 is disengaged.

Conductive Polymer

The air delivery conduit 10 can also comprise at least one conductive polymer, such as, for example, for lessening or preventing condensation formation in the conduit and/or for providing power input to a connected mask. The conductive polymer can be positioned in any suitable location, such as, for example, along the first fastening element, along the second fastening element, along one or more of the opposing longitudinal edges of the air delivery conduit, and/or through the body portion of the air delivery conduit. In one preferred embodiment, the air delivery conduit 10 comprises a conductive polymer and an insulated return wire. Additionally, it will be understood that the conductive polymer can comprise any suitable conductive material, such as, for example, a resilient and flexible conductive polymer.

Cleaning Elements

The air delivery conduit 10 can also comprise one or more cleaning elements or modules for cleaning the inside and/or outside surface of the conduit. In one embodiment, one or more cleaning elements or modules are situated (e.g., fixed) on or in a storage space (such as the storage space 30 illustrated in FIG. 9) for the conduit, such that the interior and/or exterior surface of the air delivery conduit 10 is cleaned when the conduit is pulled or pushed into or out of the storage space. Any suitable cleaning element or modules can be used in the context of the present invention. In particular, for example, the cleaning elements or modules can comprise a cleaning roller (optionally comprising a bactericide and/or fungicide) and/or a radiation-emitting device.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A fastenable air delivery conduit, comprising:
a body portion having a supply end and a delivery end; and
a fastener that substantially extends from the supply end to the delivery end,
the fastener, when engaged, forms the body portion into a fastened configuration, and when disengaged, forms the body portion into an unfastened configuration,
wherein the body portion defines a longitudinal axis when in the fastened configuration, the fastener extends from the supply end to the delivery end of the body portion at an angle that is non-parallel with the longitudinal axis of the conduit, and the fastener extends from the supply end to the delivery end of the body portion without forming a complete revolution along the fastened configuration of the body portion and wherein the conduit is convertible between said fastened and unfastened configuration.

2. The air delivery conduit of claim 1, wherein the air delivery conduit is suitable for use with a Continuous Positive Airway Pressure (CPAP) system.

3. The air delivery conduit of claim 1, wherein the body portion comprises a health grade material.

4. The air delivery conduit of claim 3, wherein the body portion comprises polyethylene.

5. The air delivery conduit of claim 1, wherein the volume of the body portion, when in the unfastened configuration, is at least about 50% less than the volume of the body portion, when in the fastened configuration.

6. The air delivery conduit of claim 1, wherein the angle formed by the fastener relative to the longitudinal axis of the air delivery conduit is less than about 40 degrees.

7. The air delivery conduit of claim 1, wherein the angle formed by the fastener relative to the longitudinal axis of the air delivery conduit is less than about 20 degrees.

8. The air delivery conduit of claim 1, wherein the fastener comprises at least one first fastening element and at least one second fastening element, wherein the at least one first fastening element is adapted to engage the at least one second fastening element.

9. The air delivery conduit of claim 1, wherein the fastener comprises a tongue-in-groove element.

10. The air delivery conduit of claim 1, wherein the fastener comprises a zipper.

11. The air delivery conduit of claim 1, wherein the body portion further comprises a conductive polymer for condensation reduction.

12. A fastenable air delivery conduit, comprising:
an unfastened body comprising first and second longitudinal edges;
a first fastener that substantially extends along the first longitudinal edge of the unfastened body; and
a second fastener that substantially extends along the second longitudinal edge of the unfastened body;
wherein the first fastener is adapted to engage the second fastener to form the unfastened body into a fastened conduit configuration
wherein the first and second fasteners comprise a tongue-in-groove arrangement, and the tongue-in-groove arrangement of the fastened conduit forms a seam extending substantially parallel to a longitudinal axis of the fastened conduit and wherein the conduit is convertible between said fastened configuration and an unfastened configuration.

13. The air delivery conduit of claim 12, wherein the air delivery conduit is suitable for use with a CPAP system.

14. The air delivery conduit of claim 12, wherein the body comprises a health grade material.

15. The air delivery conduit of claim 14, wherein the body comprises polyethylene.

16. The air delivery conduit of claim 12, wherein the volume of the air delivery conduit, when in an unfastened configuration, is at least about 50% less than the volume of the air delivery conduit, when in a fastened configuration.

17. The air delivery conduit of claim 12, wherein the unfastened body has a substantially planar configuration when in its unfastened configuration.

18. The air delivery conduit of claim 12, wherein the fastened conduit forms a tubular conduit.

19. A gas delivery system for use in CPAP therapy, comprising:
a flow generator;
a patient interface to deliver a supply of gas to a patient's face; and
a fastenable air delivery conduit comprising:
a body portion having a supply end and a delivery end adapted to be coupled respectively to the flow generator and the patient interface; and
a fastener that substantially extends from the supply end to the delivery end,
the fastener, when engaged, forms the body portion into a fastened configuration, and when disengaged, forms the body portion into an unfastened configuration,
wherein the body portion defines a longitudinal axis when in the fastened configuration, and wherein the fastener extends from the supply end to the delivery end of the body portion at an angle that is non-parallel with the longitudinal axis of the conduit and wherein the conduit is convertible between said fastened and unfastened configurations.

20. An air delivery conduit, comprising:
a body having a supply end and a delivery end, at least a portion of the body is configurable between an unfastened configuration and a fastened configuration,
wherein the body is arranged such that in the unfastened configuration at least a portion of the body may be fastened to achieve the fastened configuration, and wherein the body defines a longitudinal axis when in the fastened configuration, the body is configurable between the unfastened configuration and the fastened configuration by a fastening member along an angle that is non-parallel with the longitudinal axis, and the fastening member extends along the angle without forming a complete revolution along the body and wherein the conduit is convertible between said fastened and unfastened configurations.

21. The air delivery conduit of claim 1, wherein the body portion includes one or more structural elements disposed on an outer surface thereof.

22. The air delivery conduit of claim 1, wherein the supply end is adapted to connect to a flow generator and the delivery end is adapted to connect to a patient interface.

23. The air delivery conduit of claim 8, wherein the at least one first fastening element and the at least one second fastening element extend along opposite longitudinal edges of the body portion in the unfastened configuration.

24. The air delivery conduit of claim 12, wherein the fastened conduit includes one or more structural elements disposed on an outer surface thereof.

25. The air delivery conduit of claim 20, wherein the fastening member includes at least one first fastening element and at least one second fastening element adapted to engage one another, and wherein the at least one first fastening element and the at least one second fastening element extend along opposite longitudinal edges of the body in the unfastened configuration.

* * * * *